(12) United States Patent
Terabayashi et al.

(10) Patent No.: US 7,461,547 B2
(45) Date of Patent: Dec. 9, 2008

(54) METHODS AND APPARATUS OF DOWNHOLE FLUID ANALYSIS

(75) Inventors: Toru Terabayashi, Sagamihara (JP); Akihito Chikenji, Paris (FR); Tsutomu Yamate, Yokohama (JP); Oliver C. Mullins, Ridgefield, CT (US); Andrew L. Kurkjian, Sugar Land, TX (US); Hani Elshahawi, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/203,932

(22) Filed: Aug. 15, 2005

(65) Prior Publication Data
US 2006/0243047 A1 Nov. 2, 2006

Related U.S. Application Data

(63) Continuation-in-part of application No. 10/908,161, filed on Apr. 29, 2005.

(51) Int. Cl.
*E21B 47/08* (2006.01)
(52) U.S. Cl. .................................. 73/152.55
(58) Field of Classification Search ............. 73/152.55, 73/64.45
See application file for complete search history.

(56) References Cited

U.S. PATENT DOCUMENTS

| | | | |
|---|---|---|---|
| 3,780,575 A | 12/1973 | Urbanosky | |
| 3,859,851 A | 1/1975 | Urbanosky | |
| 3,954,006 A | 5/1976 | Anderson et al. | |
| 4,782,695 A | 11/1988 | Glotin et al. | |
| 4,860,581 A * | 8/1989 | Zimmerman et al. | 73/152.26 |
| 4,936,139 A * | 6/1990 | Zimmerman et al. | 73/152.26 |
| 4,994,671 A | 2/1991 | Safinya et al. | |
| 5,167,149 A | 12/1992 | Mullins et al. | |
| 5,201,220 A | 4/1993 | Mullins et al. | |
| 5,233,866 A | 8/1993 | Desbrandes et al. | |
| 5,266,800 A | 11/1993 | Mullins | |

(Continued)

FOREIGN PATENT DOCUMENTS

GB 2362960 5/2001

(Continued)

OTHER PUBLICATIONS

Joshi, et al., "Asphallene Precipitation from Live Crude Oil," Energy & Fuels. 2001, vol. 15., pp. 979-986, American Chemical Soc.

(Continued)

*Primary Examiner*—Hezron E. Williams
*Assistant Examiner*—Rodney T Frank
(74) *Attorney, Agent, or Firm*—Matthias Abrell; Jaime Castano; Dale Gaudier

(57) ABSTRACT

Methods and apparatus for downhole analysis of formation fluids by isolating the fluids from the formation and/or borehole in a pressure and volume control unit that is integrated with a flowline of a fluid analysis module and determining fluid characteristics of the isolated fluids. Parameters of interest may be derived for formation fluids in a static state and undesirable formation fluids may be drained and replaced with formation fluids that are suitable for downhole characterization or surface sample extraction. Isolated formation fluids may be circulated in a loop of the flowline for phase behavior characterization. Real-time analysis of the fluids may be performed at or near downhole conditions.

31 Claims, 10 Drawing Sheets

U.S. PATENT DOCUMENTS

| | | | |
|---|---|---|---|
| 5,331,156 A | 7/1994 | Hines et al. | |
| 5,549,159 A | 8/1996 | Shwe et al. | |
| 5,622,223 A | 4/1997 | Vasques et al. | |
| 5,859,430 A | 1/1999 | Mullins et al. | |
| 5,939,717 A | 8/1999 | Mullins | |
| 6,102,673 A * | 8/2000 | Mott et al. | 417/392 |
| 6,128,949 A | 10/2000 | Kleinberg et al. | |
| 6,148,912 A * | 11/2000 | Ward | 166/250.07 |
| 6,178,815 B1 | 1/2001 | Felling et al. | |
| 6,189,612 B1 * | 2/2001 | Ward | 166/250.07 |
| 6,230,824 B1 * | 5/2001 | Peterman et al. | 175/214 |
| 6,274,865 B1 | 8/2001 | Schroer et al. | |
| 6,296,056 B1 * | 10/2001 | Ward | 166/250.07 |
| 6,301,959 B1 | 10/2001 | Hrametz et al. | |
| 6,325,159 B1 * | 12/2001 | Peterman et al. | 175/7 |
| 6,343,507 B1 | 2/2002 | Felling et al. | |
| 6,467,544 B1 * | 10/2002 | Brown et al. | 166/264 |
| 6,474,152 B1 | 11/2002 | Mullins et al. | |
| 6,476,384 B1 | 11/2002 | Mullins et al. | |
| 6,585,045 B2 | 7/2003 | Lee et al. | |
| 6,609,568 B2 | 8/2003 | Krueger et al. | |
| 6,659,177 B2 * | 12/2003 | Bolze et al. | 166/264 |
| 6,688,390 B2 * | 2/2004 | Bolze et al. | 166/264 |
| 6,719,049 B2 | 4/2004 | Sherwood et al. | |
| 6,755,086 B2 * | 6/2004 | Salamitou et al. | 73/861.04 |
| 6,758,090 B2 | 7/2004 | Bostrom et al. | |
| 6,768,105 B2 | 7/2004 | Mullins et al. | |
| 6,775,996 B2 * | 8/2004 | Cowans | 62/160 |
| 6,842,700 B2 | 1/2005 | Poe | |
| 6,850,317 B2 | 2/2005 | Mullins et al. | |
| 6,854,341 B2 | 2/2005 | Oddie et al. | |
| 6,898,963 B2 | 5/2005 | Irani | |
| 7,178,591 B2 * | 2/2007 | Del Campo et al. | 166/264 |
| 2002/0112854 A1 | 8/2002 | Krueger et al. | |
| 2002/0194906 A1 | 12/2002 | Goodwin et al. | |
| 2002/0194907 A1 | 12/2002 | Bostrom et al. | |
| 2003/0033866 A1 | 2/2003 | Diakonov et al. | |
| 2004/0000433 A1 | 1/2004 | Hill et al. | |
| 2004/0000636 A1 | 1/2004 | Mullins et al. | |
| 2004/0045706 A1 | 3/2004 | Pop et al. | |

FOREIGN PATENT DOCUMENTS

| | | |
|---|---|---|
| GB | 2397382 | 7/2004 |
| WO | 02/31476 | 4/2002 |

OTHER PUBLICATIONS

Walker, I.R., "Circulation Pump for High Purity Gases at High Pressure and a Novel Linear Motor Positioning System," Rev. Sc. Instrum. 67 (2), Feb. 1996, pp. 564-578.

Sterner, Charles J., "Electromagnetic Pump for Circulating Gases at Low Flow Rates," Rev. Sc. Instruments, Oct. 1960, vol. 31, Issue 10, pp. 1159-1160.

Canfield, F.B. et al., "Electromagnetic Gas Pump for Low Temperature Service," Rev. Sci. Instrum. 34, 1431 (1963), pp. 1431-1433.

Erdman, K.L. et al., "Simple Gas Circulation Pump," Rev. Sci. Instrum. 35, 241 (1964), p. 241.

Lloyd, R.V. et al., "EPR Cavity for Oriented Single Crystals in Sealed Tubes," Rev. Sci. Instrum. 40, 514 (1969), pp. 514-515.

Mohamed, W.M. et al., "Simple High-Speed Circulating Pump for Gases," Rev. Sci. Instrum. 60 (7), Jul. 1989, pp. 1349-1350.

Duncan, S. et al., "A Double-Acting All-Glass Gas Circulating Pump," J. Sci. Instrum., 1967, vol. 44, p. 388.

Ellis, T. et al., "A Demountable Glass Circulating Pump," J. Sci. Instrum., 1962, vol. 39, pp. 234-235.

Kallo, D. et al., "Circulating Pump and Flowmeter for Kinetic Reaction Apparatus," J. Sci. Instrum., 1964, Vol. 41, pp. 338-340.

* cited by examiner

METHODS AND APPARATUS OF DOWNHOLE FLUID ANALYSIS

RELATED APPLICATION DATA

The present application claims priority under 35 U.S.C. § 120 as a continuation-in-part of U.S. Non-Provisional application Ser. No. 10/908,161 naming D. Freemark et al. as inventors, and filed Apr. 29, 2005, now pending, the aforementioned application being incorporated herein by reference in its entirety for all purposes.

FIELD OF THE INVENTION

The present invention relates to the field of analysis of downhole fluids of a geological formation for evaluating and testing the formation for purposes of exploration and development of hydrocarbon-producing wells, such as oil or gas wells. More particularly, the present invention is directed to methods and apparatus suitable for isolating formation fluids and characterizing the isolated fluids downhole utilizing, in part, a pressure and volume control unit.

BACKGROUND OF THE INVENTION

Downhole fluid analysis is an important and efficient investigative technique typically used to ascertain characteristics and nature of geological formations having hydrocarbon deposits. In this, typical oilfield exploration and development includes downhole fluid analysis for determining petrophysical, mineralogical, and fluid properties of hydrocarbon reservoirs. Fluid characterization is integral to an accurate evaluation of the economic viability of a hydrocarbon reservoir formation.

Typically, a complex mixture of fluids, such as oil, gas, and water, is found downhole in reservoir formations. The downhole fluids, which are also referred to as formation fluids, have characteristics, including pressure, temperature, volume, among other fluid properties, that determine phase behavior of the various constituent elements of the fluids. In order to evaluate underground formations surrounding a borehole, it is often desirable to obtain samples of formation fluids in the borehole for purposes of characterizing the fluids, including composition analysis, fluid properties and phase behavior. Wireline formation testing tools are disclosed, for example, in U.S. Pat. Nos. 3,780,575 and 3,859,851, and the Reservoir Formation Tester (RFT) and Modular Formation Dynamics Tester (MDT) of Schlumberger are examples of sampling tools for extracting samples of formation fluids from a borehole for surface analysis.

Formation fluids under downhole conditions of composition, pressure and temperature typically are different from the fluids at surface conditions. For example, downhole temperatures in a well could range from 300 degrees F. When samples of downhole fluids are transported to the surface, change in temperature of the fluids tends to occur, with attendant changes in volume and pressure. The changes in the fluids as a result of transportation to the surface cause phase separation between gaseous and liquid phases in the samples, and changes in compositional characteristics of the formation fluids.

Techniques also are known to maintain pressure and temperature of samples extracted from a well so as to obtain samples at the surface that are representative of downhole formation fluids. In conventional systems, samples taken downhole are stored in a special chamber of the formation tester tool and the samples are transported to the surface for laboratory analysis. During sample transfer from below surface to a surface laboratory, samples often are conveyed from one sample bottle or container to another bottle or container, such as a transportation tank. In this, samples may be damaged in the transfer from one vessel to another.

Furthermore, sample pressure and temperature frequently change during conveyance of the samples from a wellsite to a remote laboratory despite the techniques used for maintaining the samples at downhole conditions. The sample transfer and transportation procedures in use are known to damage or spoil formation fluid samples by bubble formation, solid precipitation in the sample, among other difficulties associated with the handling of formation fluids for surface analysis of downhole fluid characteristics.

In addition, laboratory analysis at a remote site is time consuming. Delivery of sample analysis data takes anywhere from a couple of weeks to months for a comprehensive sample analysis, which hinders the ability to satisfy users' demand for real-time answer products. Typically, the time frame for answer products relating to surface analysis of formation fluids is a few months after a sample has been sent to a remote laboratory.

As a consequence of the shortcomings in surface analysis of formation fluids, recent developments in downhole fluid analysis include techniques for characterizing formation fluids downhole in a wellbore or borehole. In this, the MDT may include one or more fluid analysis modules, such as the Composition Fluid Analyzer (CFA) and Live Fluid Analyzer (LFA) of Schlumberger, for example, to analyze downhole fluids sampled by the tool while the fluids are still downhole.

In downhole fluid analysis modules of the type described above, formation fluids that are to be analyzed downhole flow past a sensor module associated with the fluid analysis module, such as a spectrometer module, which analyzes the flowing fluids by infrared absorption spectroscopy, for example. In this, an optical fluid analyzer (OFA), which may be located in the fluid analysis module, may identify fluids in the flow stream and quantify the oil and water content. U.S. Pat. No. 4,994,671 (incorporated herein by reference in its entirety) describes a borehole apparatus having a testing chamber, a light source, a spectral detector, a database, and a processor. Fluids drawn from the formation into the testing chamber are analyzed by directing the light at the fluids, detecting the spectrum of the transmitted and/or backscattered light, and processing the information (based on information in the database relating to different spectra), in order to characterize the formation fluids.

In addition, U.S. Pat. Nos. 5,167,149 and 5,201,220 (both incorporated herein by reference in their entirety) describe apparatus for estimating the quantity of gas present in a fluid stream. A prism is attached to a window in the fluid stream and light is directed through the prism to the window. Light reflected from the window/fluid flow interface at certain specific angles is detected and analyzed to indicate the presence of gas in the fluid flow.

As set forth in U.S. Pat. No. 5,266,800 (incorporated herein by reference in its entirety), monitoring optical absorption spectrum of fluid samples obtained over time may allow one to determine when formation fluids, rather than mud filtrates, are flowing into the fluid analysis module. Further, as described in U.S. Pat. No. 5,331,156 (incorporated herein by reference in its entirety) by making optical density (OD) measurements of the fluid stream at certain predetermined energies, oil and water fractions of a two-phase fluid stream may be quantified.

On the other hand, samples extracted from downhole are analyzed at a surface laboratory by utilizing a pressure and volume control unit (PVCU) that is operated at ambient temperature and heating the fluid samples to formation conditions. In this, a PVCU that is able to operate with precision at high downhole temperature conditions has not been available. Conventional apparatuses for changing the volume of fluid samples under downhole conditions use hydraulic pressure with one attendant shortcoming that it is difficult to precisely control the stroke and speed of the piston under the downhole conditions due to oil expansion and viscosity changes that are caused by the extreme downhole temperatures. Furthermore, oil leakages at O-ring seals are experienced under the high downhole pressures requiring excessive maintenance of the apparatus.

SUMMARY OF THE INVENTION

In consequence of the background discussed above, and other factors that are known in the field of downhole fluid analysis, applicants discovered methods and apparatus for downhole analysis of formation fluids by isolating the fluids from the formation and/or borehole in a flowline of a fluid analysis module. In preferred embodiments of the invention, the fluids are isolated with a pressure and volume control unit (PVCU) that is integrated with the flowline and characteristics of the isolated fluids are determined utilizing, in part, the PVCU.

Advantageously, the PVCU is suitable for downhole applications and since the flowline and/or PVCU of the downhole tool are used to isolate formation fluids, undesirable formation fluids can easily be drained and replaced with formation fluids that are suitable for downhole characterization. Another advantageous result obtained by isolating formation fluids according to the present invention is that downhole pressure-volume-temperature (PVT) analysis of the fluids may be performed at or near downhole conditions utilizing the PVCU of the present invention.

Applicants recognized that there is need for downhole analyses, which provide accurate answer products in close conjunction with sampling by a downhole tool, such as a formation tester tool.

Applicants also recognized that downhole formation fluid analysis, which is reliable and comparable in scope with laboratory-based analyses, addresses known problems of formation fluid sample destruction due to transportation to the surface.

Applicants further recognized that downhole analysis obviates a delay involved in transferring formation fluid samples to a surface laboratory by providing real-time answer products at the wellsite.

Applicants discovered that fluid characterization performed on fluids that are isolated from a formation or borehole so as to be in relatively stable, static state tends to be more accurate in comparison with downhole analysis of fluids that are in an active flowing state while being characterized.

Applicants recognized that a fluid sample isolated in a tool flowline, as compared with a fluid sample captured in a sampling chamber of a downhole tool, has advantageous benefits since the isolated fluid may be checked for quality and be substituted with another, better quality isolated fluid if the quality of the initial fluid were found to be unsuitable for fluid characterization. In this, it is possible to flush a flowline of a fluid analysis module and extract fresh formation fluid for analysis while the tool is downhole whereas conventional sampling chambers and containers may not have means for draining sampled fluid and acquiring another sample of formation fluids while the tool is situated downhole.

Applicants further recognized that having an isolated fluid downhole under conditions that are substantially similar to formation or borehole conditions provides unexpected advantages in performing fluid characterization since tests such as bubble point determination require less time under downhole conditions as compared with a surface laboratory environment.

In preferred embodiments of methods and apparatus of the present invention, a tool suitable for downhole use isolates formation fluids from the formation or borehole in a flowline of the tool. Advantageously, the flowline of the tool may include a pressure and volume control unit (PVCU) that is integrated with the flowline such that pressure and volume changes to isolated formation fluids are possible under downhole conditions. The isolated formation fluids may be analyzed by measuring fluid properties, such as composition, gas-oil ratio (GOR), BTU, density, viscosity, compressibility; determining phase behavior of the fluids, such as asphaltene onset pressure, bubble point, dew point; and measuring fluid pressure and temperature values.

In one embodiment of the present invention, an apparatus for downhole fluid analysis has a plurality of devices, for example, seal valves, that can selectively be operated to stop and start flow of formation fluids in at least portions of the flowline and one or more sensors associated with a flowline of the apparatus. In one. preferred embodiment of the invention, a PVCU includes a pump, such as a syringe-type pump, that is operatively connected with the flowline such that characteristics of the formation fluids isolated in the PVCU may be varied by varying volume of the fluids.

In one preferred embodiment of the present invention, formation fluid is retained or isolated in the flowline by operation of the seal valves. Advantageously, characteristics of the isolated fluid may be determined. In one aspect of the invention, an optical sensor, for example, may measure fluid properties of interest, such as hydrocarbon composition, GOR, BTU, of the isolated formation fluid. As another aspect of the invention, a suitable device, such as a density and viscosity sensor, may measure additional fluid properties of interest, such as fluid density and viscosity. As yet another aspect of the invention, a pressure/temperature sensor (P/T gauge) may measure fluid pressure and temperature of the isolated formation fluid.

Advantageously, the PVCU may change fluid pressure by expanding volume of the formation fluid isolated inside the flowline. In yet another aspect of the invention, fluid compressibility may be measured with the changed volume and changed pressure, or fluid density change or optical absorption level change may be determined.

In yet another aspect of the present invention, fluid pressure of the isolated formation fluid may be reduced down to a certain pressure such that asphaltene is precipitated. Advantageously, optical sensors, for example, may be used to detect the asphaltene precipitation. Further decrease in pressure may cause gaseous components to separate from the liquid phase. An ultra sonic sensor and optical sensors, for example, may be used to detect outbreak of gas bubbles.

If the isolated fluid is gas condensate, when the fluid is at certain pressure condensate oil may come out from the gas condensate. For example, an optical sensor may be used to detect the condensate oil. Time dependent sensor properties may be monitored for detecting gravity segregation of the phases. After completion of the measurements of interest, the isolated fluid sample may be drained into mud, fresh formation fluid drawn into the flowline to flush out the flowline, and a sample of formation fluid may be captured in a suitable sample chamber or bottle of the downhole tool for transportation to the surface for laboratory analysis.

In accordance with the invention, a fluid analysis module of a downhole fluid characterization apparatus includes a flowline for formation fluids to flow through the fluid analysis module. At least one selectively operable device, such as a valve and/or a pump in preferred embodiments of the invention, may be provided for isolating a quantity of the fluids in the flowline. At least one sensor is located on the flowline for measuring parameters of interest relating to the fluids in the flowline.

In preferred embodiments of the invention, each of a first and second selectively operable device comprises a valve. In other embodiments of the invention, one of the selectively operable device comprises a pump, for example, in a pumpout module, and the other comprises a valve. Preferably, a pump unit, such as a syringe-type pump, integrated with the flowline is provided for varying pressure and volume of the isolated fluids.

One or more sensors, such as a spectral sensor optically coupled to the flowline; a fluorescence and gas sensor; a density sensor; a pressure sensor; a temperature sensor; a bubbles/gas sensor; a MEMS based sensor; an imager; a resistivity sensor; a chemical sensor; and a scattering sensor, are provided with respect to the flowline for characterization of formation fluids in the flowline. In preferred embodiments of the invention, a bypass flowline is provided and the selectively operable devices are structured and arranged for isolating fluids in the bypass flowline. A circulation line interconnects a first end of the bypass flowline with a second end of the bypass flowline such that isolated fluids may be circulated in the circulation line and the bypass flowline by a circulation pump.

In one preferred embodiment of the invention, one or more of a spectral detector optically coupled to the flowline; a fluorescence and gas detector; a chemical sensor; and a resistivity sensor are provided on the flowline for measuring parameters of interest relating to fluids flowing through the flowline and one or more of a density sensor; a pressure gauge; a temperature gauge; a bubbles/gas detector; a MEMS based sensor; an imager; and a scattering detector system are provided for measuring parameters of interest relating to fluids isolated in the bypass flowline.

The present invention provides a method of downhole characterization of formation fluids utilizing a downhole tool having a fluid analysis module with a flowline. The method includes monitoring at least a first parameter of interest relating to formation fluids flowing in the flowline; when a predetermined criterion for the first parameter of interest is satisfied, restricting flow of the formation fluids in the flowline by operation of a plurality of selectively operable devices to isolate formation fluids in a portion of the flowline of the fluid analysis module; and characterizing the isolated fluids by operation of one or more sensor on the flowline.

Other preferred embodiments of the method include characterizing the isolated fluids by determining one or more fluid property of the isolated fluids including, in one preferred embodiment, by changing fluid pressure of the isolated fluids by varying volume of the isolated fluids before determining the fluid property or properties, for example, one or more of fluid compressibility; asphaltene precipitation onset; bubble point; and dew point. Another preferred embodiment of the method includes circulating the isolated fluids in a closed loop of the flowline while characterizing the isolated fluids, for example, by determining phase behavior of the isolated fluids. Advantageously, time dependent sensor properties may be monitored for detecting gravity segregation of the phases.

Yet another embodiment of the present invention provides a tool for characterizing formation fluids located downhole in an oilfield reservoir. A fluid analysis module of the tool includes a flowline for formation fluids to flow through with a bypass flowline and a circulation line interconnecting a first end of the bypass flowline with a second end of the bypass flowline being provided such that fluids in the flowline may be circulated by a circulation pump. At least one sensor is situated on the bypass flowline for measuring parameters of interest relating to the fluids in the bypass flowline.

Additional advantages and novel features of the invention will be set forth in the description which follows or may be learned by those skilled in the art through reading the materials herein or practicing the invention. The advantages of the invention may be achieved through the means recited in the attached claims.

BRIEF DESCRIPTION OF THE DRAWINGS

The accompanying drawings illustrate preferred embodiments of the present invention and are a part of the specification. Together with the following description, the drawings demonstrate and explain principles of the present invention.

Figure 1:
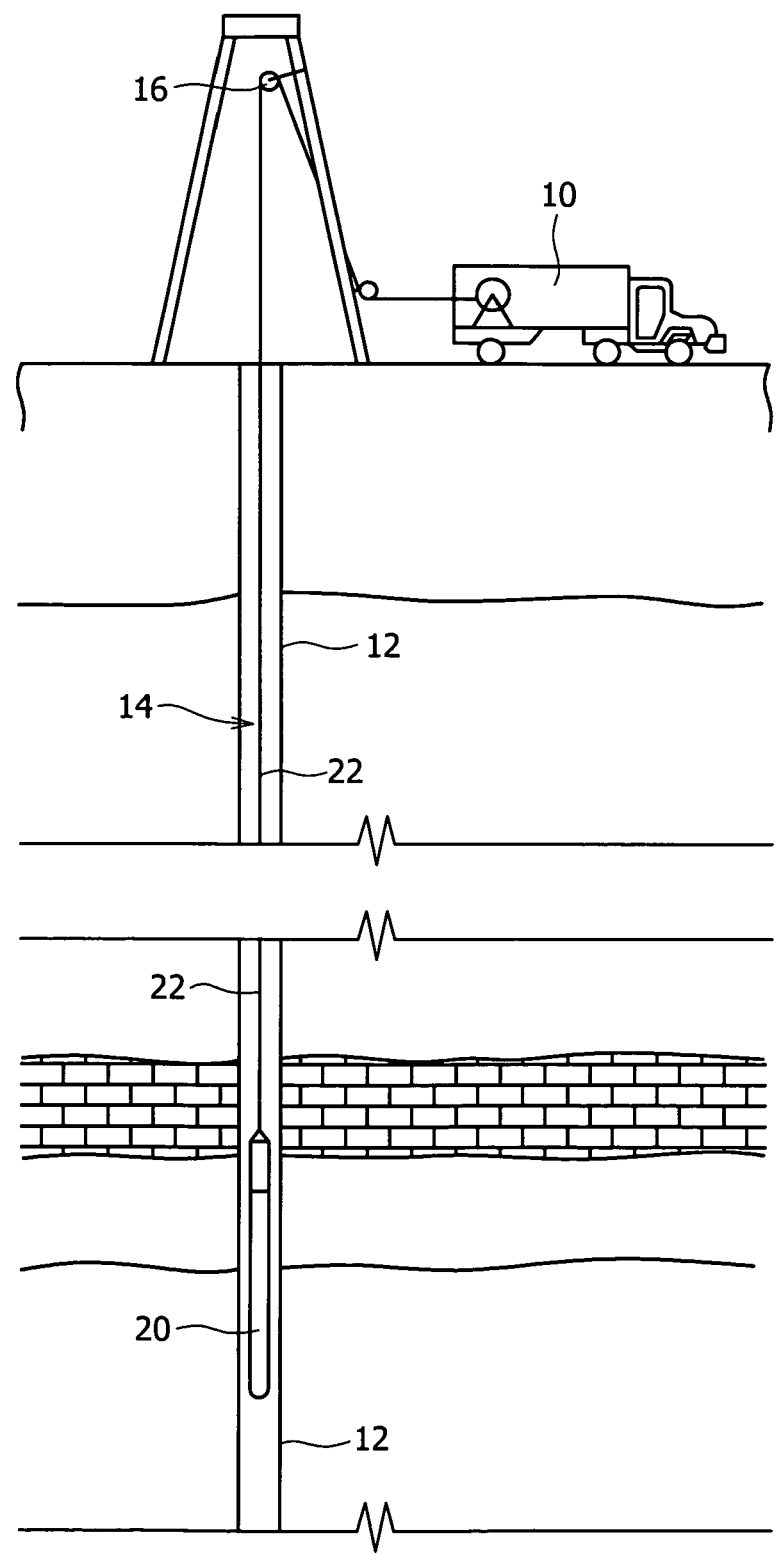
FIG. 1 is a schematic representation in cross-section of an exemplary operating environment of the present invention.

Throughout the drawings, identical reference numbers indicate similar, but not necessarily identical elements. While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the scope of the invention as defined by the appended claims.

DETAILED DESCRIPTION OF PREFERRED EMBODIMENTS

Illustrative embodiments and aspects of the invention are described below. In the interest of clarity, not all features of an actual implementation are described in the specification. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such development effort might be complex and time-consuming, but would nevertheless be a routine undertaking for those of ordinary skill in the art having benefit of the disclosure herein.

The present invention is applicable to oilfield exploration and development in areas such as downhole fluid analysis using one or more fluid analysis modules in Schlumberger's Modular Formation Dynamics Tester (MDT), for example.

FIG. 1 is a schematic representation in cross-section of an exemplary operating environment of the present invention wherein a service vehicle 10 is situated at a wellsite having a borehole or wellbore 12 with a borehole tool 20 suspended therein at the end of a wireline 22. FIG. 1 depicts one possible setting for utilization of the present invention and other operating environments also are contemplated by the present invention. Typically, the borehole 12 contains a combination of fluids such as water, mud filtrate, formation fluids, etc. The borehole tool string 20 and wireline 22 typically are structured and arranged with respect to the service vehicle 10 as shown schematically in FIG. 1, in an exemplary arrangement.

Figure 2:
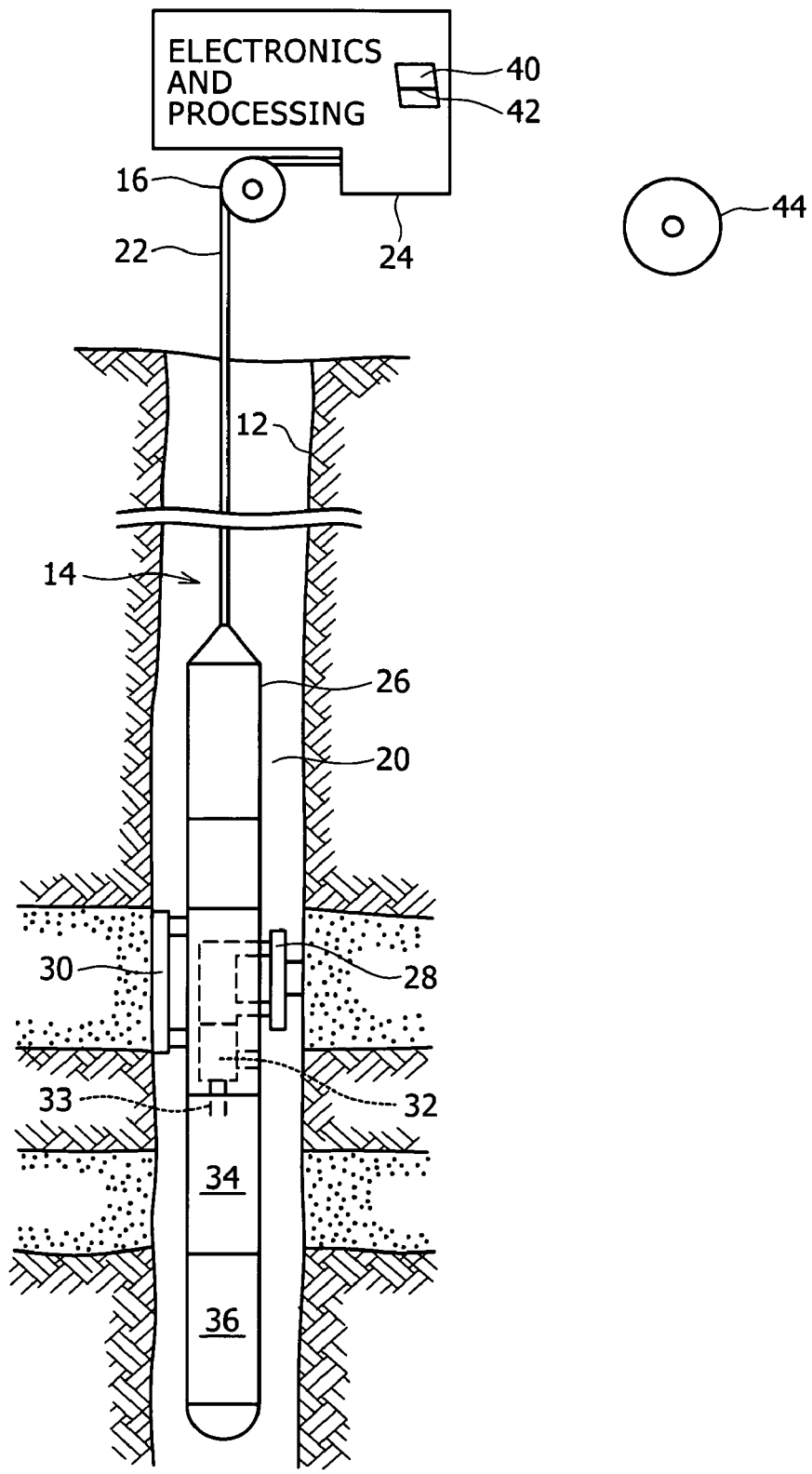
FIG. 2 is a schematic representation of one embodiment of a system for downhole analysis of formation fluids according to the present invention with an exemplary tool string deployed in a wellbore.

FIG. 2 is an exemplary embodiment of a system 14 for downhole analysis and sampling of formation fluids according to the present invention, for example, while the service vehicle 10 is situated at a wellsite (note FIG. 1). In FIG. 2, a borehole system 14 includes a borehole tool string 20, which may be used for testing earth formations and analyzing the composition of fluids from a formation. The borehole tool 20 typically is suspended in the borehole 12 (note also FIG. 1) from the lower end of a multiconductor logging cable or wireline 22 spooled on a winch 16 (note again FIG. 1) at the formation surface. The logging cable 22 typically is electrically coupled to a surface electrical control system 24 having appropriate electronics and processing systems for the borehole tool 20.

Figure 3:
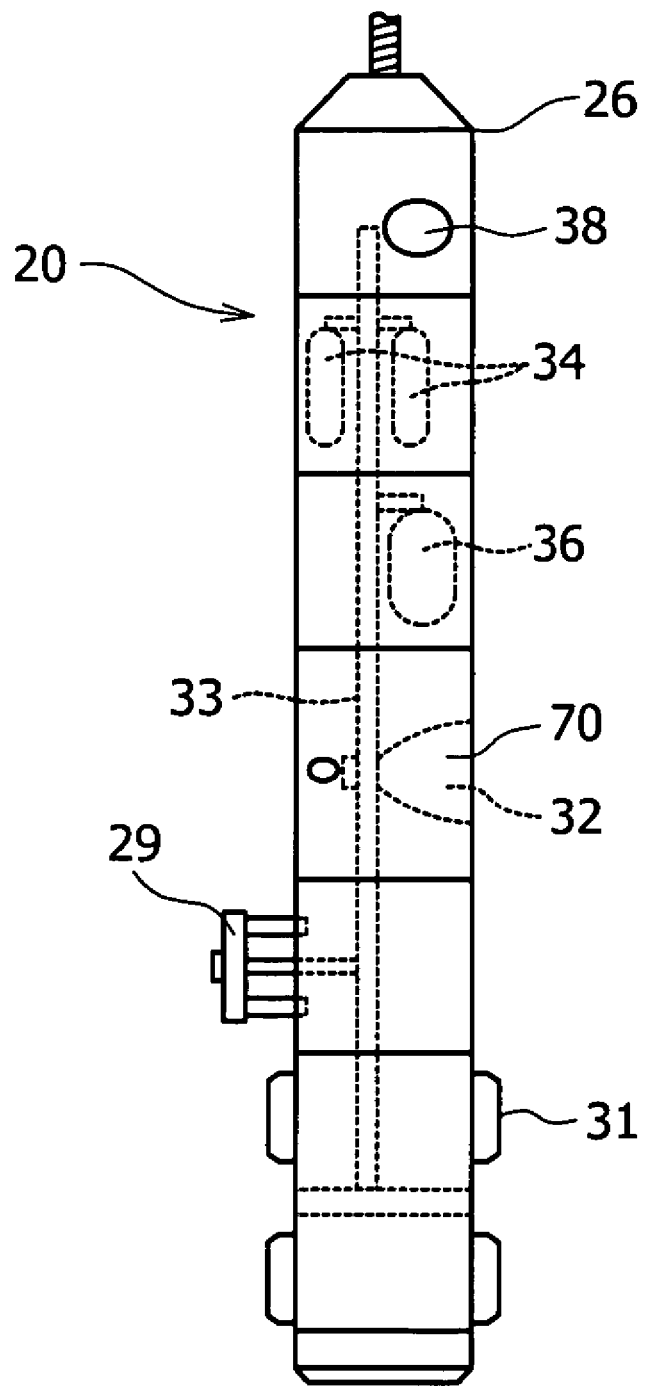
FIG. 3 shows schematically one preferred embodiment of a tool string according to the present invention with a fluid analysis module having a pressure and volume control unit (PVCU) for downhole analysis of formation fluids.

Referring also to FIG. 3, the borehole tool 20 includes an elongated body 26 encasing a variety of electronic components and modules, which are schematically represented in FIGS. 2 and 3, for providing necessary and desirable functionality to the borehole tool string 20. A selectively extendible fluid admitting assembly 28 and a selectively extendible tool-anchoring member 30 (note FIG. 2) are respectively arranged on opposite sides of the elongated body 26. Fluid admitting assembly 28 is operable for selectively sealing off or isolating selected portions of a borehole wall 12 such that pressure or fluid communication with adjacent earth formation is established. The fluid admitting assembly 28 may be a single probe module 29 (depicted in FIG. 3) and/or a packer module 31 (also schematically represented in FIG. 3). Examples of borehole tools are disclosed in the aforementioned U.S. Pat. Nos. 3,780,575 and 3,859,851, and in U.S. Pat. No. 4,860,581, the contents of which are incorporated herein by reference in their entirety.

One or more fluid analysis modules 32 are provided in the tool body 26. Fluids obtained from a formation and/or borehole flow through a flowline 33, via the fluid analysis module or modules 32, and then may be discharged through a port of a pumpout module 38 (note FIG. 3). Alternatively, formation fluids in the flowline 33 may be directed to one or more fluid collecting chambers 34 and 36, such as 1, 2¾, or 6 gallon sample chambers and/or six 450 cc multi-sample modules, for receiving and retaining the fluids obtained from the formation for transportation to the surface.

The fluid admitting assemblies, one or more fluid analysis modules, the flow path and the collecting chambers, and other operational elements of the borehole tool string 20, are controlled by electrical control systems, such as the surface electrical control system 24 (note FIG. 2). Preferably, the electrical control system 24, and other control systems situated in the tool body 26, for example, include processor capability for characterization of formation fluids in the tool 20, as described in more detail below.

The system 14 of the present invention, in its various embodiments, preferably includes a control processor 40 operatively connected with the borehole tool string 20. The control processor 40 is depicted in FIG. 2 as an element of the electrical control system 24. Preferably, the methods of the present invention are embodied in a computer program that runs in the processor 40 located, for example, in the control system 24. In operation, the program is coupled to receive data, for example, from the fluid analysis module 32, via the wireline cable 22, and to transmit control signals to operative elements of the borehole tool string 20.

The computer program may be stored on a computer usable storage medium 42 associated with the processor 40, or may be stored on an external computer usable storage medium 44 and electronically coupled to processor 40 for use as needed. The storage medium 44 may be any one or more of presently known storage media, such as a magnetic disk fitting into a disk drive, or an optically readable CD-ROM, or a readable device of any other kind, including a remote storage device coupled over a switched telecommunication link, or future storage media suitable for the purposes and objectives described herein.

In preferred embodiments of the present invention, the methods and apparatus disclosed herein may be embodied in one or more fluid analysis modules of Schlumberger's formation tester tool, the Modular Formation Dynamics Tester (MDT). The present invention advantageously provides a formation tester tool, such as the MDT, with enhanced functionality for the downhole characterization of formation fluids and the collection of formation fluid samples. In this, the formation tester tool may advantageously be used for sampling formation fluids in conjunction with downhole characterization of the formation fluids.

Figure 4:
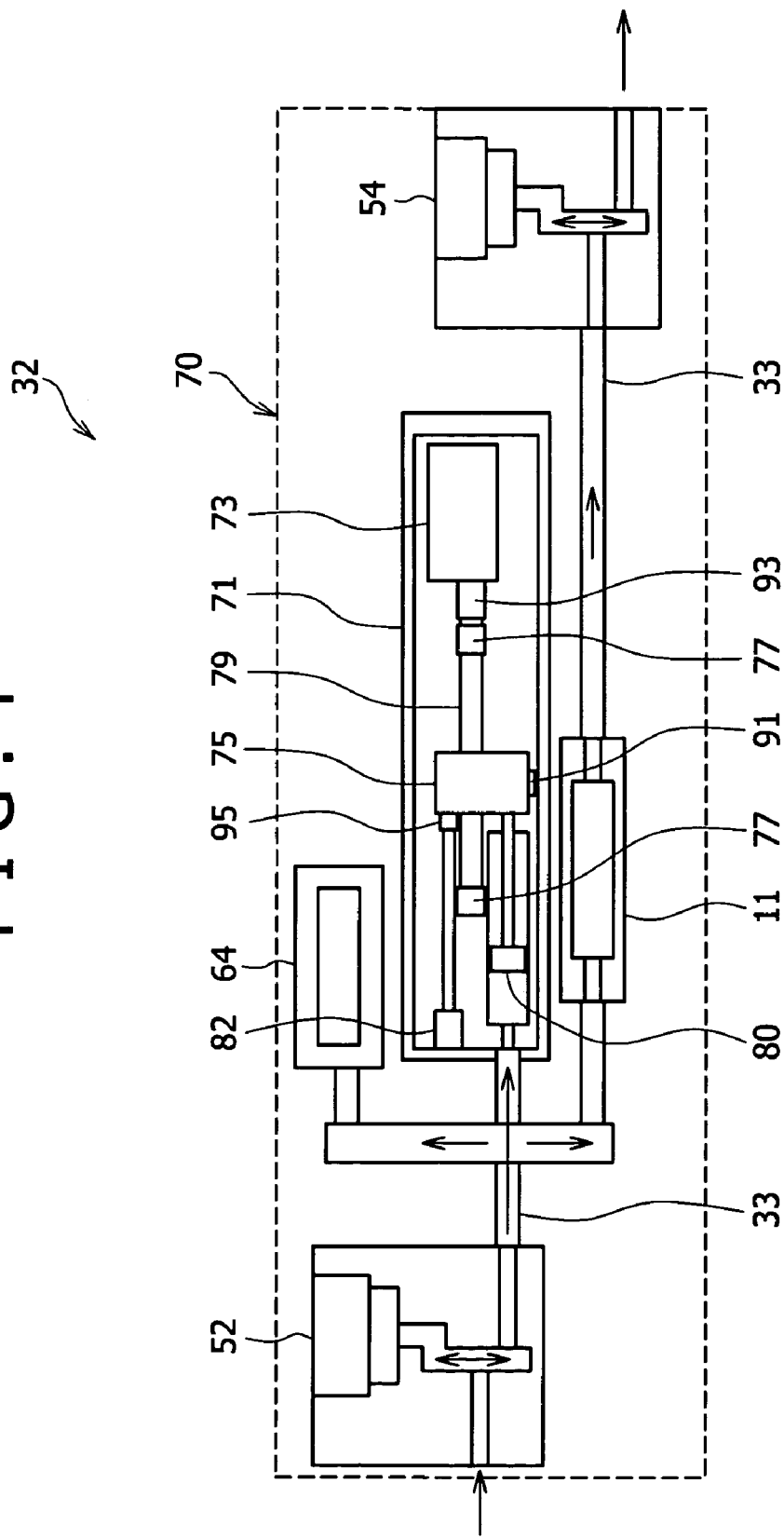
FIG. 4 shows in schematic representation one embodiment of a fluid analysis module with a PVCU apparatus according to the present invention for downhole characterization of fluids by isolating the formation fluids.

FIG. 4 is a schematic depiction of one preferred embodiment of the fluid analysis module 32 with a pressure and volume control unit (PVCU) 70 (note also FIG. 3). In preferred embodiments of the present invention, the PVCU apparatus 70 may be integrated with the flowline 33 of the module 32. One or more sensors 11 (one sensor being schematically depicted in FIG. 4 for purposes of illustration) and selectively operable devices 52 and 54 (hereinafter also generically referred to as "valves") for stopping and starting flow of fluids are operatively associated with the flowline 33. For example, as depicted in FIG. 4, the devices 52 and 54 may be seal valves having an electrically operated stepping motor with an associated piston arrangement for opening and closing the valve. In this, selectively operable devices 52 and 54 may be any suitable flow control device, such as a pump, valve, or other mechanical and/or electrical device, for starting and stopping flow of fluids in the flowline 33. One or more of the devices 52 and 54 may be situated in the fluid analysis module 32, or may be located in other adjacent modules of the tool 20, such as the pumpout module 38 (note FIG. 3). Moreover, combinations of devices may be utilized as necessary or desirable for the practice of the present invention.

The PVCU apparatus 70 includes a pump 71, such as a syringe-type pump. The pump 71 controls the volume of formation fluid in the flowline 33 between valves 52 and 54. The pump 71 has an electrical DC pulse motor 73; ball-screw 79; piston and sleeve arrangement 80 with an O-ring (not shown); motor-ball screw coupling 93; ball-screw bearings 77; and a block 75 connecting the ball screw 79 with the piston 80. Advantageously, the PVCU apparatus 70 and the pump 71 are operable at high temperatures up to 200 deg. C. The section of the flowline 33 with the inlet valve (for example, valve 52 as depicted in FIG. 4) is directly connected with the pump 71 to reduce the dead volume of the isolated formation fluid. In this, by situating the piston 80 of the pump 71 along the same axial direction as the inlet segment of the flowline 33 the dead volume of the isolated fluids is reduced since the volume of fluids left in the flowline 33 from previously sampled fluids affects the fluid properties of subsequently sampled fluids.

The flowline 33 may be branched into two directions with one branch connected to the outlet valve (valve 54 in FIG. 4) and the other connected with a pressure/temperature gauge 64 for sensing pressure/temperature characteristics of formation fluids in the flowline 33. In the embodiment depicted in FIG. 4, pump 71 has, for example, a DC stepping/pulse motor 73 with a gear to decrease the effect of backlash, ball-screw 79, piston and sleeve arrangement 80, and linear position sensor 82, such as a potentiometer. To decrease motor backlash a 1/160 reducer gear may be utilized and to precisely control position of the piston 80 a DC stepping motor with a 1.8 degree pulse may be utilized. The axis of the piston 80 may be off-set from the axis of the ball-screw 79 and the motor 73 so that total tool length is minimized.

In operation, rotational movement of the motor 73 is transferred to the axial displacement of the piston 80 through the ball-screw 79 with a guide key 91. Change in volume may be determined by the displacement value of the piston 80, which may be directly measured by an electrical potentiometer 82, for example, while precisely and changeably controlling rotation of the motor 73, with one pulse of 1.8 deg., for example. The electrical DC pulse motor 73 can change the volume of formation fluids retained in the flowline by actuating the piston 80, connected to the motor 73, by way of control electronics using position sensor signals. Since a preferred embodiment of the invention includes a pulsed motor and a high-resolution position sensor, the operation of the PVCU can be controlled with a high level of accuracy. The volume change is calculated by a surface area of the piston times the traveling distance recorded by a displacement or linear position sensor, such as a potentiometer, which is operatively connected with the piston. During the volume change, several sensors, such as pressure, temperature, chemical and density sensors and optical sensors, may measure the properties of the fluid sample captured between two seal valves 52 and 54.

When it is determined that formation fluids satisfying predetermined criteria are flowing in the flowline 33, the two seal valves 52 and 54 are closed to capture the formation fluids in the PVCU 70 under the downhole conditions. The electrical motor 73 may be actuated for changing the volume of the isolated fluids. The displacement position of the piston 80 may be directly measured by the position sensor 82, fixed via a nut joint 95 and block 75 with the piston 80, while pulse input to the motor 73 accurately control the traveling speed and distance of the piston 80. The PVCU 70 is configured based on the desired motor performance required by the downhole environmental conditions, the operational time, the reducer and the pitch of the ball-screw. After fluid characterization measurements are completed by the sensors and measurement devices of the module 32, the piston 80 is returned back to its initial position and the seal valves 52 and 54 are opened so that the PVCU 70 is ready for another operation.

Figure 5:
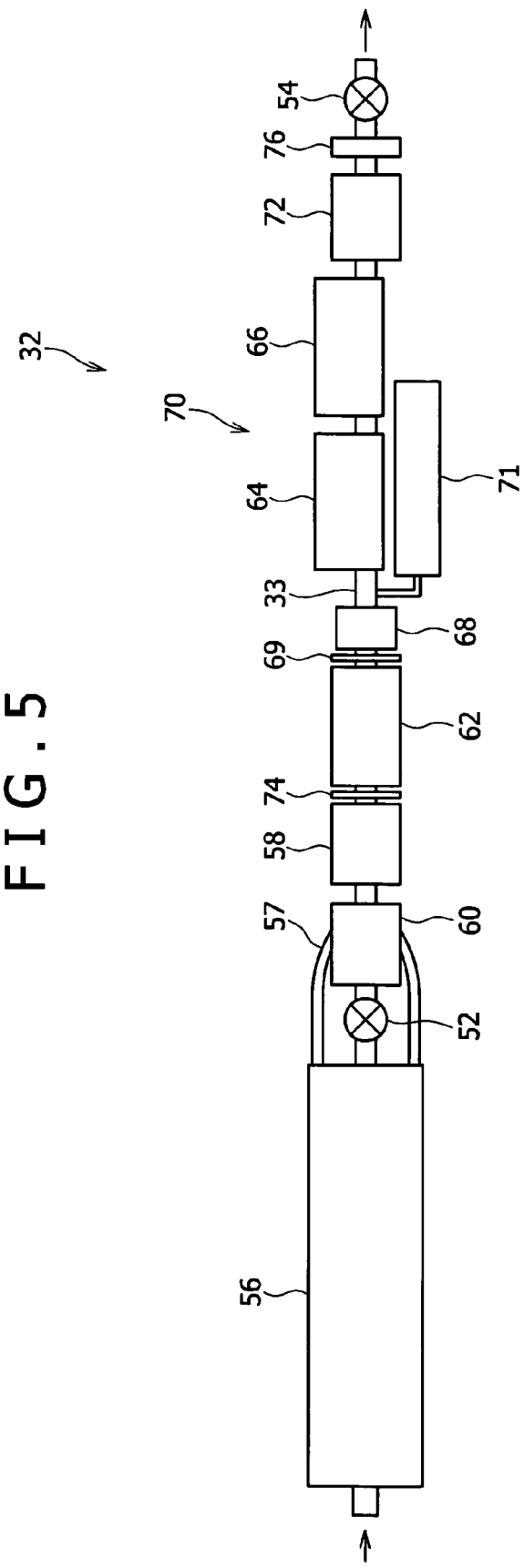
FIG. 5 is a schematic depiction of a PVCU apparatus with an array of sensors in a fluid analysis module according to one embodiment of the present invention.

FIG. 5 schematically represents one preferred embodiment of a pressure and volume control unit (PVCU) 70 having an array of sensors arranged in the fluid analysis module 32 according to the present invention. As depicted in FIG. 2, the module 32 is in fluid communication, via flowline 33, with a formation surrounding a borehole 12. Referring again to FIG. 5, in one preferred embodiment, the PVCU apparatus 70 has, for example, two seal valves 52 and 54 operatively associated with the flowline 33. The valves 52 and 54 are situated so as to control the flow of formation fluids in a segment of the flowline 33 and to isolate formation fluids in the segment of the flowline 33 between the two valves 52 and 54. According to embodiments of the present invention, valves such as high-temperature high-pressure valves suitable for downhole use may be used for controlling the flow of formation fluids in the flowline 33. For example, a throttle and seal valve may be used in accordance with the present invention.

One or more optical sensors, such as a 36 channels optical spectrometer 56, connected by an optical fiber bundle 57 with an optical cell or refractometer 60, and/or a fluorescence and gas detector 58, may be arranged on the flowline 33, to be situated between the seal valves 52 and 54. The optical sensors may advantageously be used to characterize fluids flowing through or retained in the flowline 33. U.S. Pat. Nos. 5,331,156 and 6,476,384, and U.S. Patent Application Publication No. 2004/0000636A1 (incorporated herein by reference in their entirety) disclose methods of characterizing formation fluids.

A density sensor 62 and/or pressure/temperature sensors 64 also may be provided on the flowline 33 to acquire density, pressure and/or temperature measurements with respect to fluids in the segment of the flowline 33 between seal valves 52 and 54. In this, density and/or viscosity sensors such as x-ray sensors, gamma ray sensors, vibrating rod and wire sensors, among others, may advantageously be used for fluid characterization according to embodiments of the present invention.

A resistivity sensor 74 and/or a chemical sensor 69 also may be provided on the flowline 33 to acquire fluid electrical resistance measurements and/or for detecting $CO_2$, $H_2S$, pH, among other chemical properties, with respect to fluids in the flowline 33 between seal valves 52 and 54. U.S. Pat. No. 4,860,581, incorporated herein by reference in its entirety, discloses apparatus for fluid analysis by downhole fluid pressure and/or electrical resistance measurements.

An ultra sonic transducer 66 and/or a microfabricated and microelectromechanical (MEMS) density and viscosity sensor 68 also may be provided to measure characteristics of formation fluids flowing through or captured in the flowline 33 between the valves 52 and 54. U.S. Pat. No. 6,758,090 and Patent Application Publication No. 2002/0194906A1 (incorporated herein by reference in their entirety) disclose methods and apparatus of detecting bubble point pressure and MEMS based fluid sensors, respectively.

Figure 6:
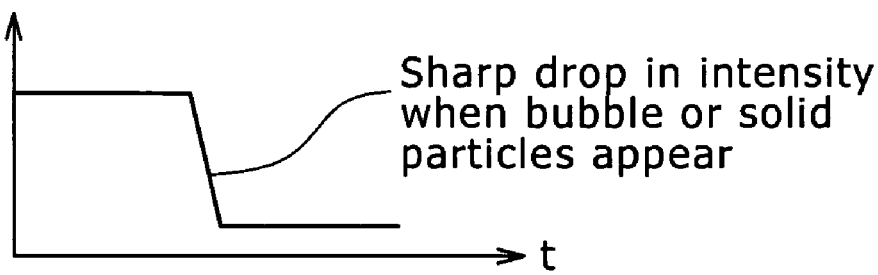
FIG. 6 is a schematic representation of a scattering detector system of the PVCU apparatus according to one embodiment of the present invention.
Figure 6:
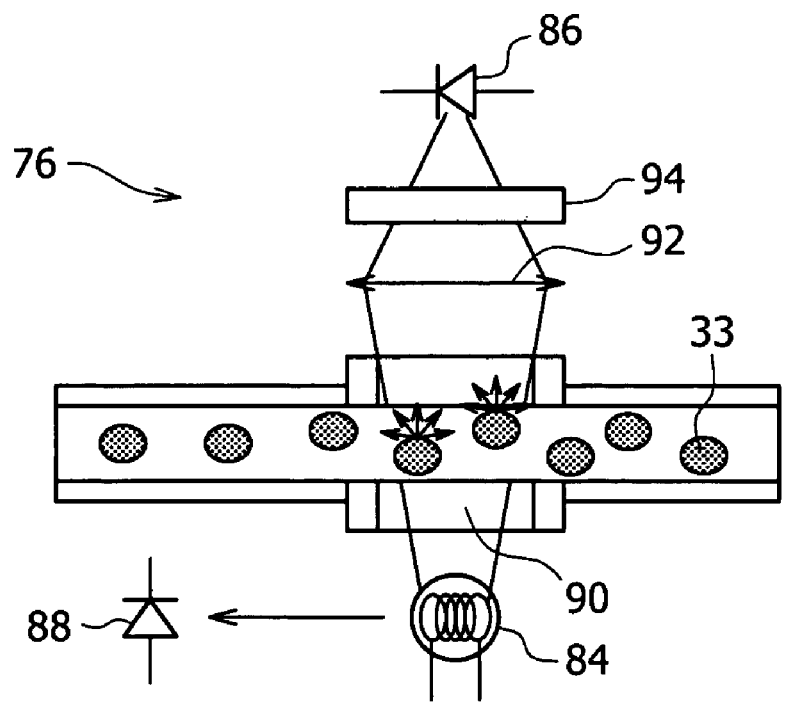

A scattering detector system 76 may be provided on the flowline 33 to monitor phase separation in the isolated fluids by detecting particles, such as asphaltene, bubbles, oil mist from gas condensate, that come out of isolated fluids in the flowline 33. FIG. 6 is a schematic representation of a scattering detector system of the apparatus 70 according to one embodiment of the present invention. Advantageously, the scattering detector 76 may be used for monitoring phase separation by bubble point detection as graphically represented in FIG. 6.

The scattering detector 76 includes a light source 84, a first photodetector 86 and, optionally, a second photodetector 88. The second photodetector 88 may be used to evaluate intensity fluctuation of the light source 84 to confirm that the variation or drop in intensity is due to formation of bubbles or solid particles in the formation fluids that are being examined. The light source 84 may be selected from a halogen source, an LED, a laser diode, among other known light sources suitable for the purposes of the present invention.

The scattering detector 76 also includes a high-temperature high-pressure sample cell 90 with windows so that light from the light source 84 passes through formation fluids flowing through or retained in the flowline 33 to the photodetector 86 on the other side of the flowline 33 from the light source 84. Suitable collecting optics 92 may be provided between the light source 84 and the photodetector 86 so that light from the light source 84 is collected and directed to the photodetector 86. Optionally, an optical filter 94 may be provided between the optics 92 and the photodetector 86. In this, since the scattering effect is particle size dependent, i.e., maximum for wavelengths similar to or lower than the particle sizes, by selecting suitable wavelengths using the optical filter 94 it is possible to obtain suitable data on bubble/particle sizes.

Referring again to FIG. 5, a pump unit 71, such as a syringe-pump unit, may be arranged with respect to the flowline 33 to control volume and pressure of formation fluids retained in the flowline 33 between the valves 52 and 54. A video imaging system 72, such as a CCD camera, may be provided on the flowline 33 for spectral imaging to characterize phase behavior of downhole fluids, as disclosed in co-pending U.S. patent application Pub. No. US 2007/0035736, titled "Spectral Imaging for Downhole Fluid Characterization", filed concurrently herewith.

Figure 7:
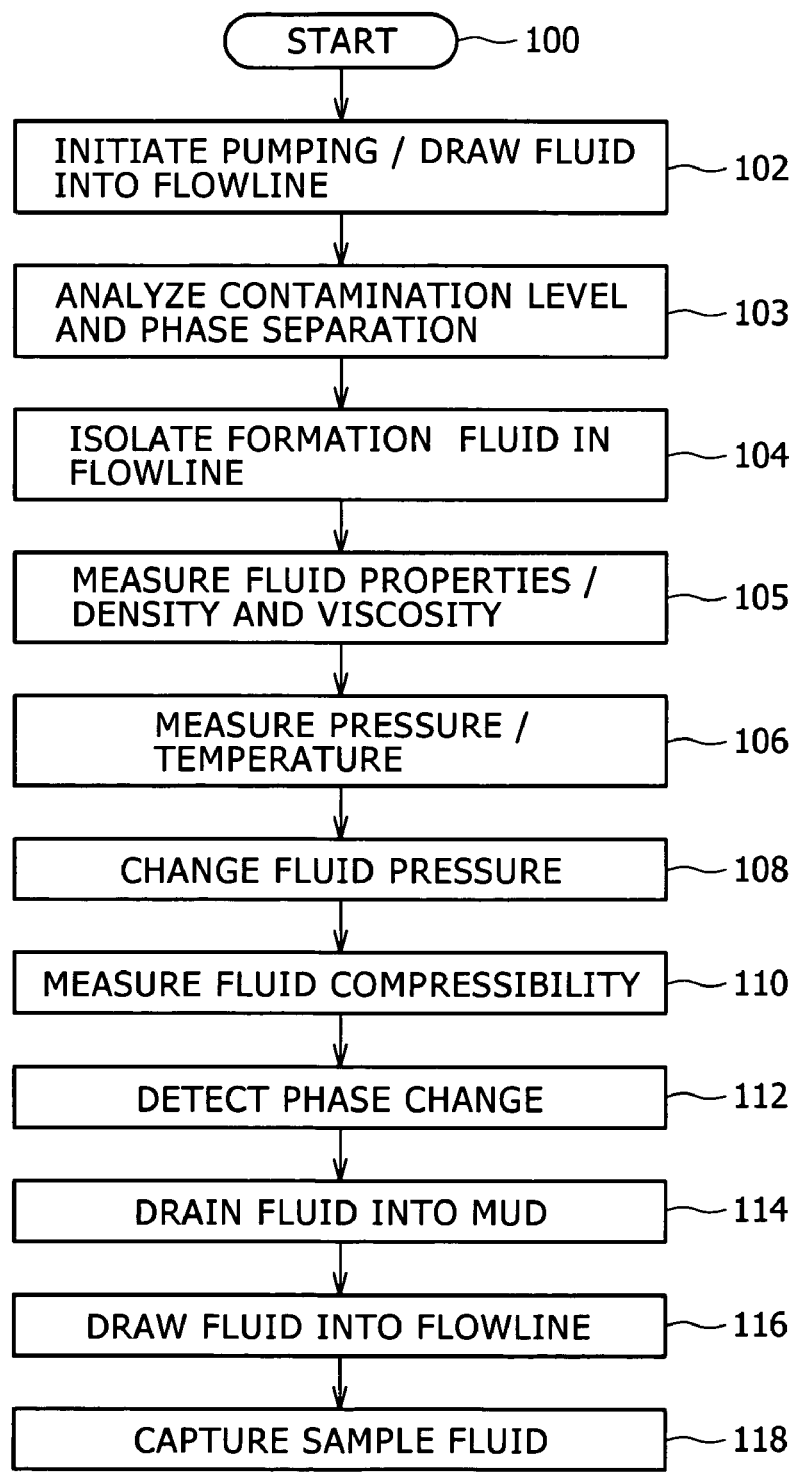
FIG. 7 represents in flowchart one method according to the present invention for downhole characterization of formation fluids.

FIG. 7 represents in flowchart one preferred method according to the present invention for downhole analysis and sampling of formation fluids, and for generating answer products of interest based on downhole fluid characterization. Referring also to FIGS. 2 and 3, when an operation of the fluid analysis module 32 is commenced (Step 100 in FIG. 7), the probe 28 is extended out from the tool string 20 to contact with the formation (note FIG. 2). Pumpout module 38 (note FIG. 3) draws formation fluid into the flowline 33 (Step 102) and drains it to the mud. The module 32 analyzes sample contamination level and phase separation (Step 103) while fluid is flowing inside the flowline 33. U.S. Pat. No. 5,266, 800, incorporated herein by reference in its entirety, discloses methods of distinguishing between a fluid containing oil base mud and formation oil samples.

Referring also to FIGS. 4 and 5, after contamination has attained a level that is determined as sufficiently low for purposes of fluid characterization and/or sample collection, for example, contamination from about 0% to about 10%, and the fluid in the flowline 33 is confirmed as single phase, the two seal valves 52 and 54 are closed so that formation fluid is isolated or trapped in the flowline 33 between the valves 52 and 54 (Step 104). The sensors and gauges of the apparatus 32 may be operated for measurements of fluid properties, such as density and viscosity of the formation fluid isolated in the flowline 33 (Step 105) and pressure and temperature (Step 106) of the isolated formation fluid.

The pump unit 71 may be operated to change pressure of the isolated fluid in the flowline 33 (Step 108). Sensors of the apparatus 32 may be operated to monitor and record fluid compressibility and phase behavior of the isolated fluid, such as asphaltene precipitation onset, bubble point, dew point, among others (Steps 110 and 112).

The video imaging system 72, such as a CCD camera, may be used to monitor asphaltene precipitation, bubble break out, and liquid separation from gas condensate. The imager 72 also may be used to measure precipitated asphaltene size change when pressure of the isolated fluid is decreasing. Aforementioned, concurrently filed, U.S. patent application Pub. No. US 2007/0035736, is directed to spectral imaging for downhole fluid characterization, the entire contents of which are incorporated herein by reference.

After completion of the measurements of interest, the isolated fluid sample may be drained into mud (Step 114). Fresh formation fluid may be drawn into the flowline to flush out the flowline (Step 116). A sample of formation fluid may be captured in a suitable sample chamber or bottle of the downhole tool for transportation to the surface for laboratory analysis (Step 118).

Figure 8:
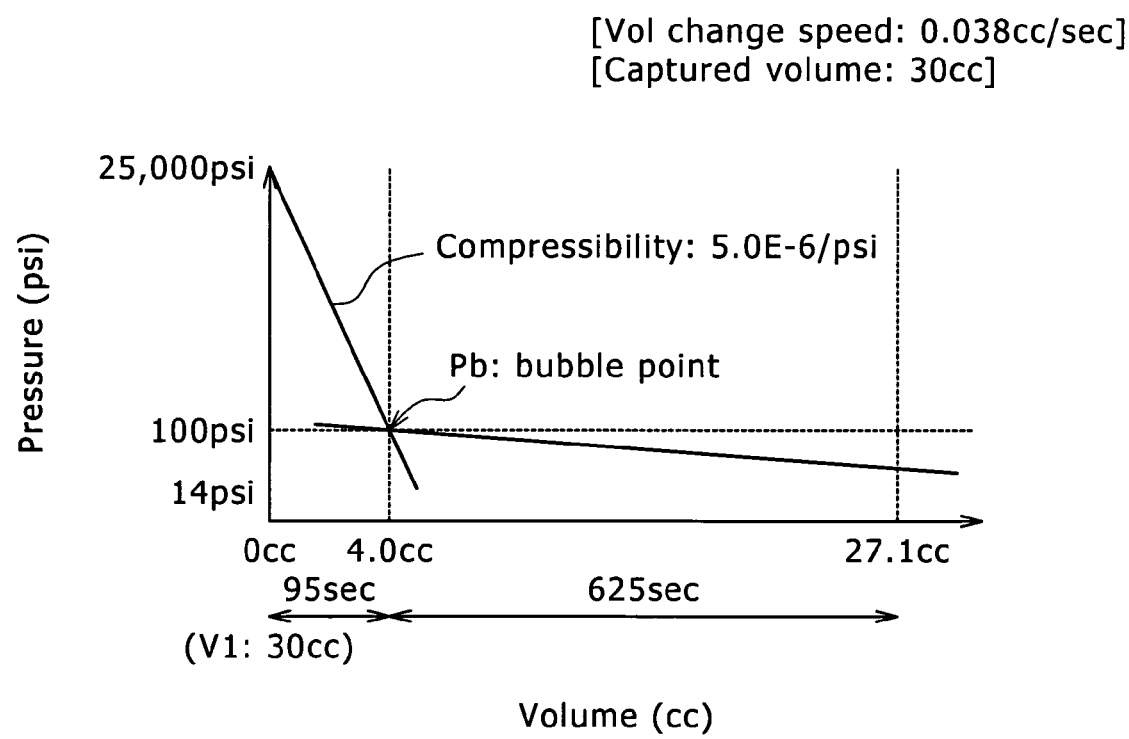
FIG. 8 graphically depicts compressibility measurement of a fluid sample according to one embodiment of the present invention.

FIG. 8 graphically depicts compressibility measurement of a fluid sample. The fluid compressibility is calculated from the initial volume, the changed volume and the decreased pressure. In this, compressibility of the fluid retained in the flowline may be calculated from decreased pressure and increased volume of the fluid derived from the displacement recorded by a displacement or position sensor, such as the potentiometer 82 (described above in connection with FIG. 4).

Figure 9:
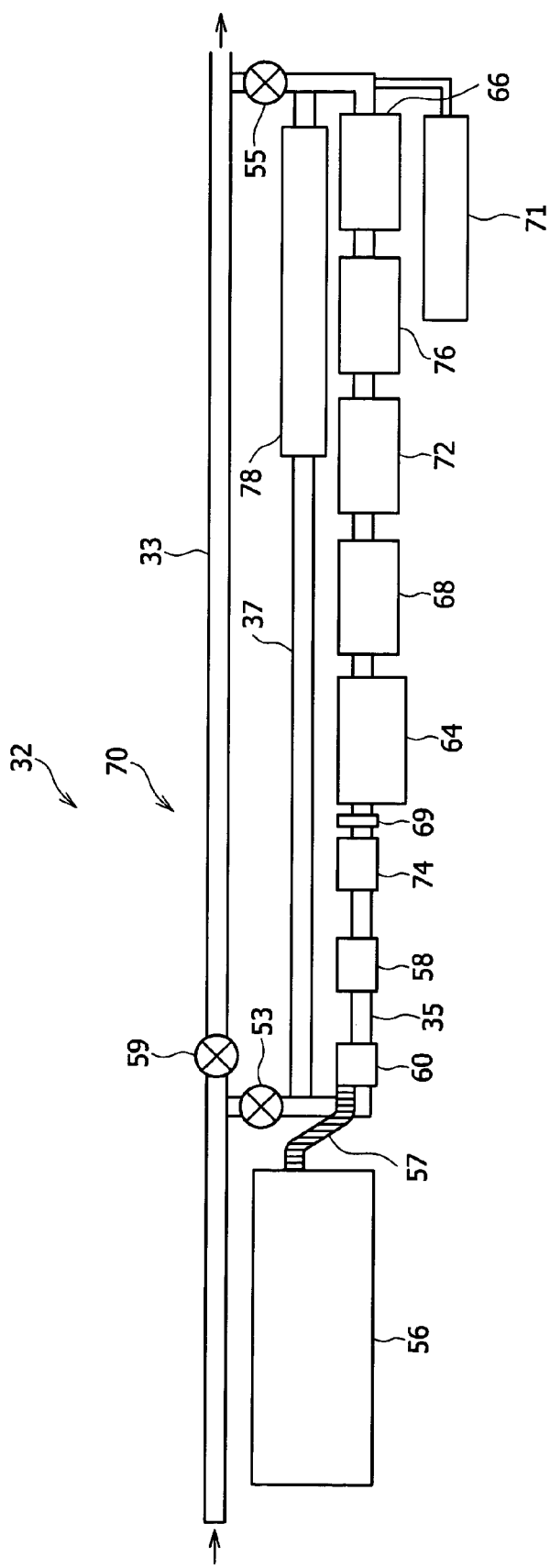
FIG. 9 shows in schematic representation another embodiment of an apparatus according to the present invention for downhole characterization of fluids.

FIG. 9 schematically represents another preferred embodiment of a fluid analysis module 32 according to the present invention. The apparatus 70 depicted in FIG. 9 includes a bypass flowline 35 and a circulation line 37 in fluid communication, via main flowline 33, with a formation surrounding a borehole. In one preferred embodiment, the apparatus 70 of FIG. 9 includes two seal valves 53 and 55 operatively associated with the bypass flowline 35. The valves 53 and 55 are situated so as to control the flow of formation fluids in the bypass flowline segment 35 of the main flowline 33 and to isolate formation fluids in the bypass flowline 35 between the two valves 53 and 55. A valve 59 may be situated on the main flowline 33 to control fluid flow in the main flowline 33.

One or more optical sensors, such as a 36 channels optical spectrometer 56, connected by an optical fiber bundle 57 with an optical cell or refractometer 60, and/or a fluorescence/refraction detector 58, may be arranged on the bypass flowline 35, to be situated between the valves 53 and 55. The optical sensors may advantageously be used to characterize fluids flowing through or retained in the bypass flowline 35.

A pressure/temperature gauge 64 and/or a resistivity sensor 74 also may be provided on the bypass flowline 35 to acquire fluid electrical resistance, pressure and/or temperature measurements with respect to fluids in the bypass flowline 35 between seal valves 53 and 55. A chemical sensor 69 may be provided to measure characteristics of the fluids, such as $CO_2$, $H_2S$, pH, among other chemical properties. An ultra sonic transducer 66 and/or a density and viscosity sensor 68 also may be provided to measure characteristics of formation fluids flowing through or captured in the bypass flowline 35 between the valves 53 and 55. A pump unit 71 may be arranged with respect to the bypass flowline 35 to control volume and pressure of formation fluids retained in the bypass flowline 35 between the valves 53 and 55. An imager 72, such as a CCD camera, may be provided on the bypass flowline 35 for spectral imaging to characterize phase behavior of downhole fluids isolated therein.

A scattering detector system 76 may be provided on the bypass flowline 35 to detect particles, such as asphaltene, bubbles, oil mist from gas condensate, that come out of isolated fluids in the bypass flowline 35. A circulation pump 78, for example, a gear pump or a Sanchez pump, may be provided on the circulation line 37. Since the circulation line 37 is a loop flowline of the bypass flowline 35, the circulation pump 78 may be used to circulate formation fluids that are isolated in the bypass flowline 35 in a loop formed by the bypass flowline 35 and the circulation line 37.

In the embodiments of the invention depicted in FIGS. 4 and 5, after formation fluid is isolated or trapped in the flowline 33, by operation of the valves 52 and 54, further flow of formation fluid in the flowline 33 is stopped. However, in some circumstances it may not be desirable to stop fluid flow in the main flowline 33 since if a valve in the main flowline 33 were to break down the job would have to be abandoned to replace the defective valve. To address such possibilities, wherein stopping fluid flow in the main flowline 33 is not a preferred approach to fluid characterization, the bypass flowline 35 of the FIG. 9 embodiment is provided and the sensors and measuring devices of the fluid analysis module 32 are situated on the bypass flowline 35. In the FIG. 9 embodiment of the invention, fluid flow may be maintained in the main flowline 33 even after formation fluid has been isolated in the bypass flowline 35. Alternatively, the valve 59 may regulate fluid flow in the main flowline 33.

Applicants have discovered that accuracy of phase behavior measurements is improved if the isolated fluid sample in the bypass flowline 35 is circulated in a closed loop line. Accordingly, the bypass flowline 35 is looped, via the circulation line 37, and circulation pump 78 is provided on the looped flowline 35 and 37 so that formation fluids isolated in the bypass flowline 35 may be circulated, for example, during phase behavior characterization.

Figure 10:
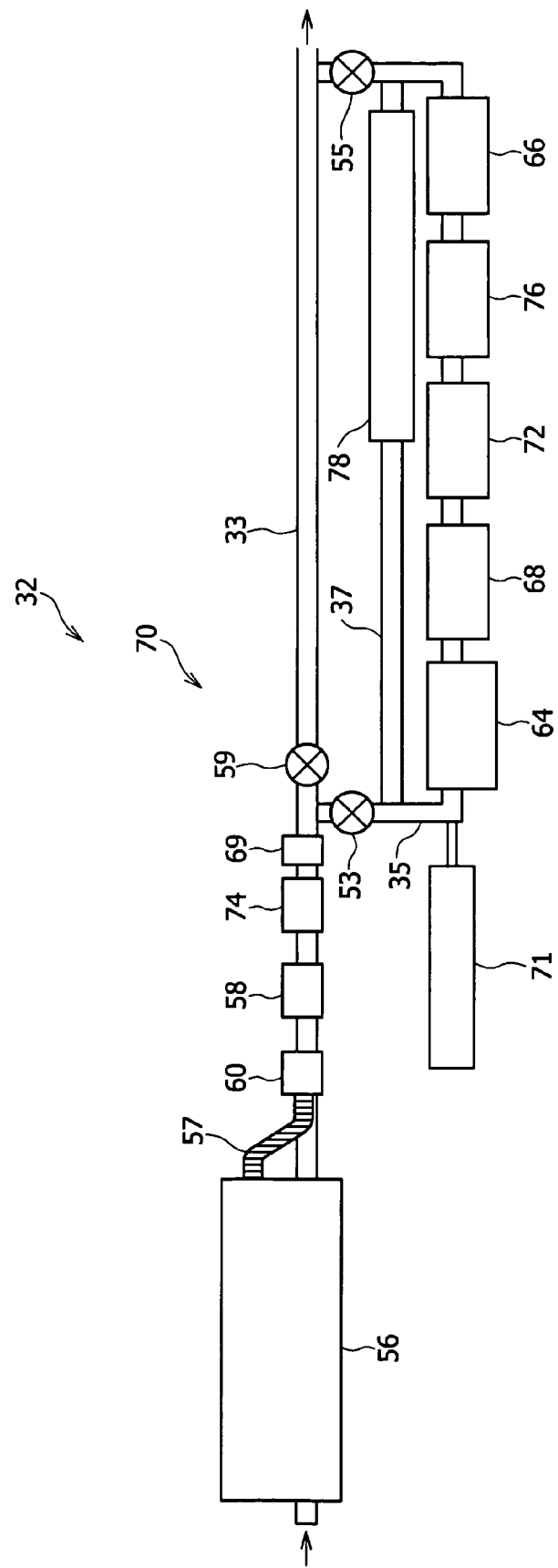
FIG. 10 shows in schematic representation yet another embodiment of an apparatus according to the present invention for downhole characterization of fluids.

FIG. 10 schematically represents yet another preferred embodiment of a fluid analysis module 32 according to the present invention. The apparatus 70 depicted in FIG. 10 is similar to the embodiment in FIG. 9 with a bypass flowline 35 and a circulation line 37 in fluid communication, via main flowline 33, with a formation surrounding a borehole. The apparatus 70 of FIG. 10 includes two valves 53 and 55 operatively associated with the bypass flowline 35. The valves 53 and 55 are situated so as to control the flow of formation fluids in the bypass flowline segment 35 of the main flowline 33 and to isolate formation fluids in the bypass flowline 35 between the two valves 53 and 55. A valve 59 may be situated on the main flowline 33 to control fluid flow in the main flowline 33.

The apparatus 70 depicted in FIG. 10 is similar to the apparatus depicted in FIG. 9 except that one or more optical sensors, such as a 36 channels optical spectrometer 56, connected by an optical fiber bundle 57 with an optical cell or refractometer 60, and/or a fluorescence/refraction detector 58, may be arranged on the main flowline 33, instead of the bypass flowline 35 as depicted in FIG. 9. The optical sensors may be used to characterize fluids that are flowing through the main flowline 33 since optical sensor measurements do not require an isolated, static fluid. Instead of the arrangement depicted in FIG. 9, a resistivity sensor 74 and a chemical sensor 69 also may be provided on the main flowline 33 in the embodiment of FIG. 10 to acquire fluid electrical resistance and chemical measurements with respect to fluids flowing in the main flowline 33.

A pressure/temperature gauge 64 may be provided on the bypass flowline 35 to acquire pressure and/or temperature measurements with respect to fluids in the bypass flowline 35 between valves 53 and 55. An ultra sonic transducer 66 and/or a density and viscosity sensor 68 also may be provided to measure characteristics of formation fluids flowing through or captured in the bypass flowline 35 between the valves 53 and 55.

A pump unit 71 may be arranged with respect to the bypass flowline 35 to control volume and pressure of formation fluids retained in the bypass flowline 35 between the valves 53 and 55. An imager 72, such as a CCD camera, may be provided on the bypass flowline 35 for spectral imaging to characterize phase behavior of downhole fluids isolated therein. A scattering detector system 76 may be provided on the bypass flowline 35 to detect particles, such as asphaltene, bubbles, oil mist from gas condensate, that come out of isolated fluids in the bypass flowline 35. Advantageously, a circulation pump 78 may be provided on the circulation line 37. Since the circulation line 37 is a loop flowline of the bypass flowline 35, the circulation pump 78 may be used to circulate formation fluids that are isolated in the bypass flowline 35 in a loop formed by the bypass flowline 35 and the circulation line 37.

The ends of the flowline 33 that extend from the fluid analysis module 32 may be connected with other modules in the formation tester tool, for example, with a CFA and/or LFA. Fluids extracted from the formation and/or borehole flow through the flowline for downhole fluid analysis by the interconnected modules. In operation of the downhole tool 20, the valves of the apparatus 70 are usually open. The sensors and gauges situated on the flowline may selectively be operated to monitor characteristics of the formation fluids passing through the flowline.

Advantageously, the methods and apparatus of the present invention have two approaches to characterization of formation fluids. One, a flowing fluid analysis and, second, an isolated or trapped fluid analysis. In this, flowing sample analysis data may be provided to a user at the surface, and also may be used for compensating and/or validating the isolated fluid analysis data.

When it is ascertained that a fluid flowing through the flowline is single phase, i.e., formation oil or water or gas with no phase separation, and a level of contamination of the fluid is confirmed as not changing and at a predetermined level for purposes of fluid property analysis, the valves 52 and 54 on the flowline 33 (note FIGS. 4 and 5) are closed and a fluid sample is isolated or trapped in the flowline. After formation fluid is isolated in a segment of the flowline, fluid properties, such as composition, GOR, and BTU, may be measured by an optical spectrometer, for example. U.S. Pat. Nos. 5,859,430 and 5,939,717, incorporated herein by reference in their entirety, disclose methods and apparatus of determining GOR and compositional analysis.

A density sensor may measure density of the isolated formation fluid. A MEMS, for example, may measure density and/or viscosity and a P/T gauge may measure pressure and temperature. A chemical sensor may detect various chemical properties of the isolated formation fluid, such as $CO_2$, $H_2S$, pH, among other chemical properties.

A pump unit connected to the flowline may increase volume of the isolated fluid sample, i.e., fluid pressure is decreased, in the flowline. When drop in pressure results in phase transition, time dependent signals may be generated in the sensors as the phases gravity separate, as further discussed in *Asphaltene Precipitation from Live Crude Oil*, Joshi, N. B. et al., Energy & Fuels 2001, 15, 979-986. In this, by monitoring sensor properties in relation to time gravity segregation may be detected.

In addition to the methods described above, compressibility of the isolated fluid also may be measured by utilizing a density sensor, optical spectrometer and pump. Fluid pressure may be decreased further so that phase behavior of the isolated fluid, such as asphaltene onset, bubble point, dew point, may be measured by a spectrometer, fluorescence and gas detector, and ultra sonic (US) transducer.

In other preferred embodiments of the present invention as depicted in FIGS. 9 and 10, the fluid analysis module 32 may be one module in a series of interconnected modules of a formation tester tool, such as Schlumberger's MDT. When a downhole job is started using the formation tester tool, a probe, such as the probe 29 in FIG. 3, is extended out from the tool 20 and attaches to the formation (note assembly 28 in FIG. 2). The tool 20 extracts formation fluid, which passes into a pressure test chamber for measurement of the formation pressure. After the pressure test is complete, the pumpout module 38 (note FIG. 3) is operated to draw formation fluid into the main flowline 33 (note FIGS. 9 and 10) and to drain the formation fluid into the borehole, i.e., into the mud surrounding the tool 20 in the borehole. Sensors and devices situated on the flowline, such as a spectrometer, fluorescence detector, resistivity sensor, and D/V sensor, monitor contamination level changes in the formation fluids that are flowing in the flowline. When contamination levels of the formation fluids reach a predetermined level, and fluid phase is verified as single phase, then the main flowline valve 59 of the module 32 (note again FIGS. 9 and 10) is closed and the bypass flowline valves 53 and 55 are opened so that formation fluid flows into the bypass flowline 35 to replace the previous fluid in the bypass flowline 35. The bypass flowline valves 53 and 55 are then closed and the valve 59 on the main flowline 33 is opened so that formation fluid is isolated or trapped in the bypass flowline 35 between the valves 53 and 55.

After isolating formation fluid in the bypass flowline 35, characteristics of the isolated formation fluid, such as density, viscosity, chemical composition, pressure, and temperature may be measured. The circulation pump 78 (note again FIGS. 9 and 10) may be operated to circulate or mix the formation fluid in the bypass flowline 35. A pump unit may be operated to increase the volume of the formation fluid isolated in the bypass flowline 35 so that pressure of the fluid is reduced. A scattering detector, US transducer, and/or CCD camera may be used to measure the bubble point of the isolated formation fluid.

During the pressure-volume-temperature (PVT) analysis of the isolated formation fluid, or after the PVT analysis has been completed, a sample of the formation fluid may be captured in one or more sampling chambers, such as 34 and 36 in FIG. 3, for surface analysis. Then the tool 20 may be moved to the next test point in the formation.

In conventional methods and apparatus, a formation fluid sample is collected downhole and then transported to a laboratory at the surface for analysis. In this, typically a special sampling chamber or container is necessary to maintain sample pressure and temperature at downhole conditions so as to avoid damage and spoilage of the formation fluid sample. Moreover, sample analysis conditions at a surface laboratory are different from downhole conditions causing unpredictable and unacceptable variations in analytical results, and erroneous answer products derived from the formation fluid analysis.

Advantageously, the present invention obviates need for a specialized chamber to store or analyze the formation fluids. The flowline of a downhole formation tester tool, through which formation fluids flow during normal operation of the downhole tool, may advantageously be used to isolate formation fluids for fluid characterization downhole. Furthermore, the same flowline may be used to change fluid conditions for measuring additional fluid properties and phase behavior of the isolated formation fluids.

The preceding description has been presented only to illustrate and describe the invention and some examples of its implementation. It is not intended to be exhaustive or to limit the invention to any precise form disclosed. Many modifications and variations are possible in light of the above teaching.

The preferred aspects were chosen and described in order to best explain principles of the invention and its practical applications. The preceding description is intended to enable others skilled in the art to best utilize the invention in various embodiments and aspects and with various modifications as are suited to the particular use contemplated. It is intended that the scope of the invention be defined by the following claims.

What is claimed is:

1. A downhole fluid sampling and characterization apparatus configured for operation downhole, within a borehole, comprising:
   a fluid sampling and analysis module, the fluid sampling and analysis module comprising:
   a flowline for fluids withdrawn from a formation to flow through the fluid sampling and analysis module downhole, within a borehole, the flowline having a first end for the fluids to enter and a second end for the fluids to exit the fluid sampling and analysis module;
   a first selectively operable device and a second selectively operable device structured and arranged with respect to the flowline for isolating a quantity of the fluids in a portion of the flowline between the first and second selectively operable device; and
   a pump unit integrated with the flowline for varying pressure and volume of the isolated fluids wherein the pump unit comprises a syringe-type pump; and
   at least one sensor connected to the portion of the flowline between the first and second selectively operable device for measuring parameters of interest downhole, within a borehole, relating to the fluids in the flowline.

2. The downhole fluid sampling and characterization apparatus accordingly to claim 1, wherein the least one sensor comprises a plurality of sensors.

3. The downhole fluid sampling and characterization apparatus according to claim 1, wherein the at least one sensor comprises one or more of a spectral sensor optically coupled to the flow-line; a fluorescence and gas sensor; a density sensor; a pressure sensor; a temperature sensor; a bubble/gas sensor; a MEMS based sensor; an imager; a resistivity sensor; a chemical sensor; and a scattering sensor.

4. A downhole fluid sampling and characterization apparatus configured for operation downhole, within a borehole, comprising:
   a fluid sampling and analysis module, the fluid sampling and analysis module comprising:
   a flowline for fluids withdrawn from a formation to flow through the fluid sampling and analysis module downhole, within a borehole, the flowline having a first end for the fluids to enter and a second end for the fluids to exit the fluid sampling and analysis
   a first selectively operable device and a second selectively operable device structured and arranged with respect to the flowline for isolating a quantity of the fluids in a portion of the flowline between the first and second selectively operable device; and
   at least one sensor connected to the portion of the flowline between the first and second selectively operable device for measuring parameters of interest downhole, within a borehole, relating to the fluids in the flowline, wherein;

the portion of the flowline for isolating the fluids comprising:

a bypass flowline, the first and second selectively operable device being structured and arranged for isolating fluids in the bypass flowline, and a circulation line interconnecting a first end of the bypass flowline with a second end of the bypass flowline such that fluids isolated between the first and second selectively operable device can circulate in a closed loop formed by the circulation line and the bypass flowline; and the fluid analysis module further comprising:

a circulation pump for circulating fluids in the closed loop of the circulation line and the bypass flowline.

5. The downhole fluid sampling and characterization apparatus according to claim 4, wherein the at least one sensor comprises one or more of a density sensor; a pressure sensor; a temperature sensor; a bubble/gas sensor; a MEMS based sensor; an imager; and a scattering sensor, wherein the at least one sensor measures parameters of interest relating to fluids isolated in the bypass flowline; and the fluid analysis module further comprising:

one or more of a spectral sensor optically coupled to the flowline; a fluorescence and gas sensor: a chemical sensor; and a resistivity sensor, structured and affanged with respect to the flowline for measuring parameters of interest relating to fluids flowing through the flowline.

6. A method of downhole sampling and characterization of formation fluids utilizing a downhole tool comprising a fluid analysis module positioned within a borehole having a flowline for flowing formation fluids through the fluid analysis module, the method comprising:

monitoring at least a first parameter of interest relating to formation fluids flowing in the flowline downhole, within a borehole;

when a predetermined criterion for the first parameter of interest is satisfied, restricting flow of the formation fluids in the flowline downhole by operation of a first selectively operable device and a second selectively operable device of the fluid analysis module to isolate formation fluids in a portion of the flowline of the fluid analysis module downhole between the first and second selectively operable device; and characterizing the isolated fluids by operation downhole of one or more sensor on the flowline between the first and second selectively operable device.

7. The method of downhole sampling and sampling and characterization of formation fluids according to claim 6, wherein characterizing the isolated fluids includes determining downhole one or more fluid property of the isolated fluids.

8. The method of downhole sampling and characterization of formation fluids according to claim 6 further comprising:

circulating the isolated fluids in a closed loop of the flowline while characterizing the isolated fluids.

9. A method of downhole sampling and characterization of formation fluids utilizing a downhole tool comprising a fluid analysis module positioned within a borehole having a flowline for flowing formation fluids through the fluid analysis module, the method comprising:

monitoring at least a first parameter of interest relating to formation fluids flowing in the flowline;

when a predetermined criterion for the first parameter of interest is satisfied, restricting flow of the formation fluids in the flowline by operation of a first selectively operable device and a second selectively operable device of the fluid analysis module to isolate formation fluids in a portion of the flowline of the fluid analysis module between the first and second selectively operable device; and characterizing the isolated fluids including determining one or more fluid property of the isolated fluids by operation of one or more sensor on the flowline between the first and second selectively operable device including changing fluid pressure of the isolated fluids by varying volume of the isolated fluids before determining one or more fluid property.

10. The method of downhole of sampling and characterization of formation fluids according to claim 9 further comprising:

monitoring time dependent signals in the one or more sensor on the flowline to detect gravity separation of the isolated fluids.

11. The method of downhole sampling and characterization of formation fluids according to claim 9, wherein the one or more fluid property determined after changing fluid pressure includes one or more of fluid compressibility; asphaltene precipitation onset; bubble point; and dew point.

12. A method of downhole sampling and characterization of formation fluids utilizing a downhole tool comprising a fluid analysis module positioned within a borehole having a flowline for flowing formation fluids through the fluid analysis module, the method comprising:

monitoring at least a first parameter of interest relating to formation fluids flowing in the flowline;

when a predetermined criterion for the first parameter of interest is satisfied, restricting flow of the formation fluids in the flowline by operation of a first selectively operable device and a second selectively operable device of the fluid analysis module to isolate formation fluids in a portion of the flowline of the fluid analysis module between the first and second selectively operable device; and characterizing the isolated fluids by operation of one or more sensor on the flowline between the first and second selectively operable device including determining phase behavior of the isolated fluids while circulating the fluids in the closed loop and circulating the isolated fluids in a closed loop of the flowline while characterizing the isolated fluids.

13. The method of downhole sampling and characterization of formation fluids according to claim 12, wherein determining phase behavior of the isolated fluids comprises monitoring time dependent sensor properties to detect gravity separation of the phases.

14. A tool configured to be located downhole for sampling and characterizing formation fluids located downhole in an oilfield reservoir, comprising;

a fluid analysis module, the fluid analysis module comprising:

a flowline for fluids withdrawn from a formation downhole to flow through the fluid analysis module, the flowline having a first end for the fluids to enter and a second end for the fluids to exit the fluid analysis module;

the flowline comprising;

a bypass flowline and a circulation line interconnecting a first end of the bypass flowline with a second end of the bypass flowline such that fluids can circulate in the circulation line and the bypass flowline; and the fluid analysis module further comprising:

a circulation pump for circulating fluids in the circulation line and the bypass flowline;

at least one sensor situated on the bypass flowline for measuring parameters of interest relating to the fluids in the bypass flowline; and a first selectively operable device and a second selectively operable device structured and alTanged with respect to the flowline for isolating a quantity of the fluids in the bypass flowline between the first and second selectively operable device the at least one sensor comprises one or more of a density sensor; a pressure sensor; a temperature sensor; a bubble/gas sensor; a MEMS based sensor; an imager; and a scattering sensor, wherein the at least one sensor measures parameters of interest relating to fluids isolated in the bypass flowline; and the fluid analysis module further comprising:

one or more of a spectral sensor optically coupled to the flowline; a fluorescence and gas sensor, a chemical sensor; and a resistivity sensor; structured and arranged with respect to the flowline for measuring parameters of interest relating to fluids flowing through the flowline.

15. The tool configured to be located downhole for sampling and characterization formation fluids in accordance with claim 14, wherein at least one of the first and second selectively operable device comprises a valve; and the fluid analysis module further comprising:

a pump unit integrated with the flowline for varying pressure and volume of the isolated fluids.

16. A downhole fluid sampling and characterization apparatus configured for operation downhole, within a borehole, comprising:

a fluid sampling and analysis module, the fluid sampling and analysis module comprising:

a flowline for fluids withdrawn from a formation to flow through the fluid sampling and analysis module downhole, within a borehole, the flowline having a first end for the fluids to enter and a second end for the fluids to exit the fluid sampling and analysis module;

a bypass flowline connected to said flowline for receiving fluids from said flowline for sampling and analysis;

a first selectively operable valve positioned within said bypass flowline at an initial end of said bypass flowline and a second selectively operable valve positioned within said bypass flowline at an outlet end of said bypass flowline and arranged with respect to the bypass flowline for isolating a quantity of the fluids in a portion of the bypass flowline between the first and second selectively operable valves; and at least one sensor connected to the portion of the bypass flowline between the first and second selectively operable device for measuring parameters of interest downhole, within a borehole, relating to the fluids in the flowline wherein the at least one sensor comprises at least one of:

an optical spectrometer and an optical cell, an optical spectrometer and a refractometer, a fluorescence refraction detector, an imager, a scattering detector for detecting particles within the bypass line, and an ultrasonic transducer.

17. The downhole fluid sampling and characterization apparatus according to claim 16, wherein the at least one sensor comprises:

a resistivity sensor.

18. The downhole fluid sampling and characterization apparatus according to claim 16, wherein the at least one sensor comprises:

a chemical sensor.

19. The downhole fluid sampling and characterization apparatus according to claim 16, wherein the at least one sensor comprises:

a pressure gauge.

20. The downhole fluid sampling and characterization apparatus according to claim 16, wherein the at least one sensor comprises:

a temperature gauge.

21. The downhole fluid sampling and characterization apparatus according to claim 16, wherein the at least one sensor comprises:

a density sensor.

22. The downhole fluid sampling and characterization apparatus according to claim 16, wherein the at least one sensor comprises:

a viscosity sensor.

23. The downhole fluid sampling and characterization apparatus according to claim 16, wherein the imager comprises:

a CCD camera.

24. The downhole fluid sampling and characterization apparatus according to claim 16, wherein the scattering detector for detecting particles comprises detecting at least one of:

asphaltene within the bypass flowline, bubbles within the bypass flowline, and oil mist from gas condensate within the bypass flowline.

25. A downhole fluid sampling and characterization apparatus configured for operation downhole, within a borehole, comprising:

a fluid sampling and analysis module, the fluid sampling and analysis module comprising:

a flowline for fluids withdrawn from a formation to flow through the fluid sampling and analysis module downhole, within a borehole, the flowline having a first end for the fluids to enter and a second end for the fluids to exit the fluid sampling and analysis module;

a bypass flowline connected to said flowline for receiving fluids from said flowline for sampling and analysis;

a first selectively operable valve positioned within said bypass flowline at an initial end of said bypass flowline and a second selectively operable valve positioned within said bypass flowline at an outlet end of said bypass flowline and arranged with respect to the bypass flowline for isolating a quantity of the fluids in a portion of the bypass flowline between the first and second selectively operable valves;

at least one sensor connected to the portion of the bypass flowline between the first and second selectively operable device for measuring parameters of interest downhole, within a borehole, relating to the fluids in the flowline;

a circulation line connected at one end to said bypass flowline downstream of the first valve positioned within said bypass flowline and upstream of the second valve positioned within said bypass flowline; and a circulation pump connected in series with said circulation line for circulating fluid within said bypass flowline.

26. A downhole fluid sampling and characterization apparatus configured for operation downhole, within a borehole, comprising:

a fluid sampling and analysis module, the fluid sampling and analysis module comprising:

a flowline for fluids withdrawn from a formation to flow through the fluid sampling and analysis module downhole, within a borehole, the flowline having a first end for the fluids to enter and a second end for the fluids to exit the fluid sampling and analysis module;

a bypass flowline connected to said flowline for receiving fluids from said flowline for sampling and analysis;

a first selectively operable valve positioned within said bypass flowline at an initial end of said bypass flowline and a second selectively operable valve positioned within said bypass flowline at an outlet end of said bypass flowline and arranged with respect to the bypass flowline for isolating a quantity of the fluids in a portion of the bypass flowline between the first and second selectively operable valves;

at least one sensor connected to the portion of the bypass flowline between the first and second selectively operable device for measuring parameters of interest downhole, within a borehole, relating to the fluids in the flowline; and at least another sensor connected in series with the flowline for fluids withdrawn from a formation.

27. The downhole fluid sampling and characterization apparatus according to claim 26, wherein the at least another sensor comprises:

an optical spectrometer and an optical cell.

28. The downhole fluid sampling and characterization apparatus according to claim 26, wherein the at least another sensor comprises:

an optical spectrometer and a refractometer.

29. The downhole fluid sampling and characterization apparatus according to claim 26, wherein the at least another sensor comprises:

a fluorescence refraction detector.

30. The downhole fluid sampling and characterization apparatus according to claim 26, wherein the at least another sensor comprises:

a resistivity sensor.

31. The downhole fluid sampling and characterization apparatus according to claim 26, wherein the at least another sensor comprises:

a chemical sensor.

* * * * *